(12) United States Patent
Byrd

(10) Patent No.: US 6,905,707 B2
(45) Date of Patent: Jun. 14, 2005

(54) CONTROLLED RELEASE ARGININE ALPHA KETOGLUTARATE

(75) Inventor: Edward A. Byrd, San Francisco, CA (US)

(73) Assignee: Medical Research Institute, San Francisco, CA (US)

( * ) Notice: Subject to any disclaimer, the term of this patent is extended or adjusted under 35 U.S.C. 154(b) by 473 days.

(21) Appl. No.: 10/226,646

(22) Filed: Aug. 23, 2002

(65) Prior Publication Data

US 2003/0039690 A1 Feb. 27, 2003

Related U.S. Application Data

(63) Continuation-in-part of application No. 09/755,890, filed on Jan. 5, 2001, now Pat. No. 6,572,888, which is a continuation-in-part of application No. 09/288,245, filed on Apr. 8, 1999, now Pat. No. 6,197,340, which is a continuation-in-part of application No. 09/112,623, filed on Jul. 9, 1998, now abandoned.

(60) Provisional application No. 60/102,605, filed on Oct. 1, 1998, and provisional application No. 60/087,203, filed on May 28, 1998.

(51) Int. Cl.$^7$ ........................... A61K 9/20; A61K 9/22; A61K 31/195; A61K 31/205

(52) U.S. Cl. ...................... 424/468; 424/464; 424/465; 514/557; 514/561

(58) Field of Search ................................ 424/464, 465, 424/468; 514/557, 561

(56) References Cited

U.S. PATENT DOCUMENTS

| | | | |
|---|---|---|---|
| 3,577,551 A | 5/1971 | Murakami et al. | |
| 4,461,759 A | 7/1984 | Dunn | |
| 4,520,009 A | 5/1985 | Dunn | |
| 4,705,867 A | 11/1987 | Giray et al. | |
| 4,800,044 A | 1/1989 | Giray et al. | |
| 4,966,732 A | 10/1990 | Giray et al. | |
| 5,334,612 A | 8/1994 | Kalden et al. | |
| 5,376,382 A | 12/1994 | Goede et al. | |
| 5,455,264 A | 10/1995 | Beisswenger et al. | |
| 5,505,962 A | 4/1996 | Sparks | |
| 5,527,539 A | 6/1996 | Sarlikiotis et al. | |
| 5,532,269 A | 7/1996 | Koltringer | |
| 5,569,670 A | 10/1996 | Weischer et al. | |
| 5,599,835 A | 2/1997 | Fischer | |
| 5,616,345 A | 4/1997 | Geoghegan et al. | |
| 5,637,320 A | 6/1997 | Bourke et al. | |
| 5,641,515 A | 6/1997 | Ramtoola | |
| 5,641,745 A | 6/1997 | Ramtoola | |
| 5,646,187 A | * 7/1997 | Vinnars et al. ............. | 514/557 |
| 5,650,429 A | 7/1997 | Conrad et al. | |
| 5,691,379 A | 11/1997 | Ulrich et al. | |
| 5,693,664 A | 12/1997 | Wessel et al. | |
| 5,705,192 A | 1/1998 | Bethge et al. | |
| 5,728,735 A | 3/1998 | Ulrich et al. | |
| 5,730,988 A | 3/1998 | Womack | |
| 5,827,643 A | 10/1998 | Conrad et al. | |
| 6,197,340 B1 | * 3/2001 | Byrd et al. ................. | 424/468 |
| 6,572,888 B2 | * 6/2003 | Byrd .......................... | 424/468 |

FOREIGN PATENT DOCUMENTS

| | | |
|---|---|---|
| WO | WO 89/03688 | 5/1989 |
| WO | WO 8903688 A1 * | 5/1989 |
| WO | WO 98/57627 | 12/1998 |

OTHER PUBLICATIONS

Armstrong et al., *Free Radical Biology and Chemistry,* (1996) 21(5):719–726.
Barbiroli et al., *J Neurol,* (1995) 242:472–477.
Baur et al., *Klin Wochenschr,* (1991) 69:722–724.
Bilich et al., *I–Pharmacodynamics,* (1978) 88:93.
Black et al., *Clinical and Experimental Pharmacology and Physiology,* (1998) 25:712–714.
Bloomgarden, *Diabetes Care,* (Apr. 1997) 20(4):670–673.
Burkart et al., *Agents Actions,* (1993) 38:60–65.
Busse et al., *Arzneim–Forsch/Drug Research* (1992) 42(6):829–831.
Bustamante et al., *Free Radical Biology and Medicine,* (1998) 24(6):1023–1039.
Carreau, *Methods in Enzymology,* (1979) 62:152–158.
Cesolari et al., *Rev Exp Enf Ap Digest,* (1988) 73(3) 229–232.
Chen et al., *Archives of Biochemistry and Biophysics,* (1997) 338(2):165–172.
Chokroverty et al., *Neurology,* 35(5):652–9 (1985).
Cynober, *Curr Opin Clin Nutr Metab Care,* 2(1):33–7 (1999).
Devasgayam et al., *Chem–Biol Interactions,* (1993) 86:79–92.
Dimpfel et al., *Dev Pharmacol Ther,* (1990) 14:193–199.

(Continued)

*Primary Examiner*—Thurman K. Page
*Assistant Examiner*—S. Tran
(74) *Attorney, Agent, or Firm*—Karl Bozicevic; Bozicevic, Field & Francis LLP

(57) ABSTRACT

An oral formulation of arginine α-ketoglutarate is disclosed which formulation is comprised of arginine α-ketoglutarate and one or more excipient materials. A wide range of different controlled release formulations will be apparent to those skilled in the art upon reading this disclosure. The formulation of arginine α-ketoglutarate and excipient material is designed to obtain a desired result, e.g. attenuate symptoms suffered by a patient with a glutamate dehydrogenase deficiency or increase prolyl hydroxylase and lysyl hydroxylase activity or prevent protein glycation characteristic of atheroscloerosis, cataract formation, retinopathy, and aging. The desired results are obtained by increasing the period of time that a therapeutic level of arginine α-ketoglutarate is continuously maintained in the patient. The therapeutic level as well as the period of time over which that level must be maintained can vary between patient based on a range of factors such as the condition of the patient and the patient's reactivity to arginine α-ketoglutarate. However, the period of time will be greater than that obtained with a conventional quick release arginine α-ketoglutarate formulation.

14 Claims, No Drawings

OTHER PUBLICATIONS

Egan et al., *Prostaglandins*, (1978) 16(6):861–869.
Estrada et al., *Diabetes*, (Dec. 1996) 45:1798–1804.
Faust et al., *J. Immunopharmac*, (1994) 16(1):61–66.
Fuchs et al., *Skin Pharmacol*, (1994) 7:278–284.
Gandhi et al., *J Biosci*, (Sep. 1985) 9 (1 & 2):117–127.
Garrett et al., *Neuroscience Letters*, (1997) 222:191–194.
Gerbitz et al., *Diabetes*, (Feb. 1996) 45:113–126.
Hammarqvist et al., *Crit Care Med*, (1997) 25(1):78–84.
Haugaard et al., *Biochem Biophys Acta*, (1970) 222:583–586.
Henricksen et al., *American Physiological Society*, (1990) C648–C653.
Henricksen et al., *Life Sciences*, (1997) 61(8):805–812.
Hofmann et al., *Archives of Biochemistry and Biophysics*, (1995) 324(1): 85–92.
Jacob et al., *Diabetes*, (1995) 245–250.
Jacob et al., *Diabetes*, (Aug. 1996) 45:1024–1029.
Kagan et al., *Biochemical Pharmacology*, (1992) 44(8):1637–1649.
Kagan et al., *Journal of Lipid Research*, (1992) 33:385–397.
Kagan et al., *Free Rad Res Comms*, (1991) 15(5):265–276.
Khamaisi et al., *Metabolism*, (Jul. 1997) 45(7):763–768.
Kuttan, *J. Nutr.*, 110(8):1525–32 (1980).
Lavis et al., *The Journal of Biologic Chemistry*, (Jan. 10, 1970) 245(1):23–31.
Lodge et al., *Journal of Applied Nutrition*, (1997) 49 (1 & 2)3–11.
Lodge et al., *Free Radical Biology & Medicine*, (1998) 25(3):287–297.
Matsugo et al., *Biochemistry and Molecular Biology International*, (Oct. 1995) 37(2)375–383.
Merin et al., *FEBS Letters*, (1996) 294:9–13.
Muller et al., *Toxicology*, (1989) 58:175–185.
Muller et al., *Biochimica et Biophysica Acta*, (1990) 1052:386–389.
Muller et al., *Journal of Cerebral Blood Flow and Metabolism*, (1995) 15:624–630.
Muting et al., *MMW Munch Med Wochenschr*, 119(16):538–8 (1977).
Nagamatsu et al., *Diabetes Care*, (1995) 18(8):1160–1167.
National Diabetes Data Group Classification and Diagnosis of Diabetes Mellitus and Other Categories of Glucose Intolerance, *Diabetes* (1979) 28:1039–1057.
Natraj et al., *J Biosci*, (1984) 6(1):38–46.
Nickander et al., *Free Radical Biology & Medicine* (1996) 21(5): 631–639.
Ohmori et al., *Japan J. Pharmacol*, (1986) 42:275–2.
Ohmori et al., *Japan J. Pharmacol*, (1986) 42:135–140.
Ou et al., *Free Rad Res*, (1996) 25(4):337–346.
Ou et al., *Biochemical Pharmacology*, (1995) 50(1):123–126.
Packer et al., *Free Radical Biology & Medicine*, (1997) 22(1/2): 359–378.
Packer et al., *Free Radical Biology & Medicine*, (1995) 19(2): 227–250.
Packer, *Diabetologica*, (1993) 36:1212–1213.
Pascoe et al., *Free Radical Biology & Medicine*, (1989) 6:209–224.
Peinado et al., *Archives of Biochemistry and Biophysics*, (Sep. 1989) 273(2):389–395.
Plaitakis et al., *Ann Neurol*, 7(4):297–303 (1980).
Podda et al., *Biochemical Pharmacology*, (1996) 52:627–633.
Prehn et al., *Journal of Cerebral Blood Flow and Metabolism* (1992) 12:78–87.
Reed et al., *Science*, (1951) 93–94.
Roy et al., *Biochemical Pharmacology*, (1997) 53:393–399.
Scheer et al., *Archives of Biochemistry and Biophysics*, (May 1, 1993) 302(2):385–390.
Schmid et al., *FASEB Journal*, (Jul. 1998) 12:863–870.
Schonheit et al., *Biochimica et Biophysica Acta*, (1995) 1271:335–342.
Segermann et al., *Arzneim.–Forsch/Drug Res.*, (1991) 41(12):1294–1298.
Sen et al., *The FASEB Journal*, (May 1996) 10:709–720.
Sen et al., *Free Radical Biology & Medicine*, (1997) 22(7):1241–1257.
Sen et al., *Biochemical and Biophysical Research Communications* (1998) 247:223–238.
Simopoulos, *Nutrition Today*, (Jan./Feb. 1994) 12–16.
Stoll et al., *Pharmacology Biochemistry and Behavior*, (1993) 46:799–805.
Streeper et al., *American Physiological Society*, (1997) 273(1):E185–E191.
Sumathi et al., *Jpn J Med Sci Biol*, (1996) 49:39–48.
Suzuki et al., *Free Rad Res Commsii*, (1992) 17(3):211–217.
Suzuki et al., *Biochemical and Biophysical Research Communications*, (Dec. 1992) 189(3):1709–1715.
Suzuki et al., *Free Rad Res Comms*, (1991) 15(5) 255–263.
Szabo et al., *Klin Wochenschr*, (1986) 64(Suppl. VII):116–122.
Teichert et al., *Methods in Enzymology*, (1997) vol. 279.
Wagh et al., *J. Biosci*, (Mar. 1987) 11(1):59–74.
Wagh et al., *J. Biosci*, (Jun. 1986) 10(2):171–179.
Wagner et al., *Properties and Derivatives of α–Lipoic Acid*, (Oct. 5, 1956) 5079–5081.
Wickramasinghe et al., *Biochemical Pharmacology*, (1992) 43(3) 407–411.
Witt et al., *Journal of Chromatography B*, (1998) 705:127–131.
Wolz et al., *Neuropharmacology*, (1996) 35(3):369–375.
Ziegler et al., *Deutsch Medizinische Wochenschritt*, (Jul. 1, 1988) 113(26) 1071–1074.
Ziegler et al., *Diabetologia*, (1995) 38:1425–1433.
Zimmer et al., *J Mol Cell Cardiol*, (1995) 27:1895–1903.

* cited by examiner

CONTROLLED RELEASE ARGININE ALPHA KETOGLUTARATE

CROSS REFERENCES

This application is a continuation-in-part application of Ser. No. 09/755,890, filed Jan. 5, 2001 now U.S. Pat. No. 6,572,888, which is a continuation-in-part of earlier filed patent application Ser. No. 09/288,245, filed Apr. 8, 1999 now issued U.S. Pat. No. 6,197,340, which is a continuation-in-part of earlier filed provisional patent application Ser. No. 60/102,605, filed Oct. 1, 1998 and patent application Ser. No. 09/112,623, filed Jul. 9, 1998 now abandoned, which is the converted patent application of provisional patent application Ser. No. 60/087,203, filed May 28, 1998 to which we claim priority under 35 U.S.C. §120 and §119(e) each of which is incorporated herein by reference in their entirety.

FIELD OF THE INVENTION

The present invention relates generally to a controlled release oral formulation of pharmaceutically active compounds. More particularly, the invention relates to controlled release oral formulations of salts of arginine particularly arginine α-ketoglutarate.

BACKGROUND OF THE INVENTION

Arginine α-ketoglutarate, also known as arginine 2-oxoglutarate, is an organic salt which possesses a number of physiological uses. Studies conducted in 1977 revealed its ability to enhance hepatic detoxification capacity when administered in high dosage to patients with liver cirrhosis. (Muting et al. (1977) *MMW Munch Med Wochenschr,* 119 (16):535–8.) Its effects were marked by a significant decrease in the level of plasma ammonia and free serum phenols, which indicate improved oxidative decomposition of these compounds. Likewise, administration of arginine and α-ketoglutarate has also proven useful in treating ammonia intoxication and heightening liver detoxication in animal models. Not only was the survival rate found to be higher in the treatment group relative to the control, the treatment group also suffered fewer convulsive episodes.

In addition, arginine α-ketoglutarate has various uses as a source of α-ketoglutarate. By virtue of its role in the amino acid synthesis pathway, α-ketoglutarate exerts strong regulatory control over protein metabolism. Previous studies demonstrated its potency in conserving endogenous glutamine pools and increasing glutamine synthesis, which have particular benefits in clinical nutrition and metabolic care by countering trauma-induced catabolism. (Cynober (1999) *Curr Opin Clin Nutr Metab Care,* 2(1):33–7.) U.S. Pat. No. 5,646,187 describes the utility of α-ketoglutarate in treating critically ill patients for improving protein synthesis capacity, preserving lean body mass and maintaining energy status in skeletal muscle. Similarly, WO 89/03688 discloses the use of α-ketoglutarate to increase glutamine content in postoperative patients.

Alpha-ketoglutarate also possesses antioxidative properties, as supported by studies on hydrogen peroxide ($H_2O_2$)-induced hemolysis of human erythrocytes. The non-enzymatic oxidative decarboxylation of alpha-keto acids is shown to be involved in the hydrogen peroxide decomposition process. As part of the pathway leading to the citric acid cycle, α-ketoglutarate is crucial to energy generation. Studies in this area have yielded a significant correlation between leukocyte glutamate dehydrogenase deficiency and the presence of extrapyramidal signs, supranuclear palsy, absence of osteotendineal reflexes and neurogenic electromyographical findings. (Orsi et al. (1988) *Acta Neurol Scand,* 78(5):394–400.)

Furthermore, there is a significant link between genetic deficiency of glutamate dehydrogenase, an enzyme which converts glutamate to α-ketoglutarate, and certain dominantly inherited ataxias and olivopontocerebellar atrophy (OPCA). (Plaitakis et al. (1980) *Ann Neurol,* 7(4):297–303, Chokroverty et al. (1985) *Neurology,* 35(5):652–9.) Ataxia is a condition characterized by failure of motor control and/or irregularity of muscular action whereas OPCA refers to a group of ataxias characterized by progressive neurological degeneration affecting the cerebellum, the pons and the inferior olives.

In collagen synthesis, α-ketoglutarate plays an important role as one of the cofactors of prolyl hydroxylase and lysyl hydroxylase, enzymes responsible for hydroxylation of proline and lysine residues. Studies conducted on scorbutic animal models which characteristically exhibit lowered prolyl hydroxylase activity indicate that the enzyme activity could be increased by incubating homogenates with ascorbate (Vitamine C), ferrous ions, and α-ketoglutarate thereby alleviating the pathological symptoms. (Kuttan (1980) *J Nutr,* 110(8):1525–32.)

Alpha-ketoglutarate is also highly effective in preventing glycosylation/glycation of proteins associated with diabetic complications such as atherosclerosis, cataract formation, and retinopathy, and mere aging. Protein-bound advanced glycation endproducts (AGEs) can exert cytotoxic effects on neighboring cells and are, for example, the structural components of beta-amyloid plaques in Alzheimer's disease. Administration of α-ketoglutarate, however, attenuates the cytotoxicity of these AGEs via the compound's competitive inhibition of protein glycation and antioxidant properties. In the case of diabetic retinopathy, even careful monitoring of blood glucose levels does not necessarily preclude pathogenesis. Therefore, the intake of α-ketoglutarate is required in addition to a diabetic drug to prevent the glycation process in retinopathy.

SUMMARY OF THE INVENTION

An oral formulation of arginine α-ketoglutarate is disclosed which formulation is comprised of arginine α-ketoglutarate and one or more excipient materials. A wide range of different controlled release formulations will be apparent to those skilled in the art upon reading this disclosure. The formulation of arginine α-ketoglutarate and excipient material is designed to obtain a desired result, e.g. attenuate symptoms suffered by a patient with a glutamate dehydrogenase deficiency or increase prolyl hydroxylase and lysyl hydroxylase activity or prevent protein glycation characteristic of atheroscloerosis, cataract formation, retinopathy, and aging. The desired results are obtained by increasing the period of time that a therapeutic level of arginine α-ketoglutarate is continuously maintained at a desired therapeutic level in the patient. The therapeutic level as well as the period of time over which that level must be maintained can vary between patient based on a range of factors such as the condition of the patient and the patient□s reactivity to arginine α-ketoglutarate. However, the period of time will be greater than that obtained with a conventional quick release arginine α-ketoglutarate formulation.

The ratio of arginine α-ketoglutarate to excipient material and the particular excipients used result in a formulation which allows the arginine α-ketoglutarate to be released in a controlled manner for absorption into the circulatory system. By maintaining a desired serum level of arginine α-ketoglutarate in blood serum the oral formulation of the invention achieves physiological effects which are superior to those which might be obtained when higher serum levels are obtained for a short term with a quick release oral dosage formulation or a single dose injectable formulation.

By providing for controlled release of arginine α-ketoglutarate the physiological effects are continually provided over a period of time resulting in obtaining a range of associated health benefits. The controlled release formulation of the invention shows that highly desirable therapeutic effects can be obtained by maintaining a therapeutic arginine α-ketoglutarate blood serum level over a period of time which is meaningfully longer than that obtained with a quick release formulation and results are improved by maintaining such day after day. A formulation of the invention will preferably maintain therapeutic levels of arginine α-ketoglutarate over a period which is 10% or more, more preferably 50% or more and still more preferably 100% or more than the period of time maintained by a quick release formulation.

To obtain a particularly preferred result, the oral formulation of the invention will quickly release a sufficient amount of arginine α-ketoglutarate so as to quickly obtain a therapeutic level and thereafter release arginine α-ketoglutarate at a rate which substantially matches the rate at which the arginine α-ketoglutarate is being metabolized. Accordingly, the formulation is designed to maintain a therapeutic level over a maximum amount of time based on the amount of arginine α-ketoglutarate in the formulation and to not significantly exceed the therapeutic level.

An aspect of the invention is an oral formulation of arginine α-ketoglutarate, and excipient compounds which provide for controlled release.

A more specific aspect of the invention is that the formulation protects arginine α-ketoglutarate from degradation and allows it to be slowly released over time.

An advantage of the invention is that by maintaining relatively low serum levels of arginine α-ketoglutarate over long periods of time, protein glycation can be inhibited, thereby preventing the onset of atherosclerosis, cataracts, retinopathy, and adverse effects of aging.

Another advantage of the invention is that by administering the formulation over longer periods, the patient is provided with a reduced risk of developing atherosclerosis, diseases of the eye and adverse conditions associated with aging.

Another aspect of the invention is that the formulation provides a method of enhancing prolyl hydroxylase and lysyl hydroxylase activity.

Yet another aspect of the invention is that the formulation provides a method of treating symptoms of dominant ataxias arising from glutamate dehydrogenase deficiency.

An advantage of the invention is that a convenient oral delivery dosage form is used to obtain the results which are superior to a single injectable dose.

A feature of the invention is that the oral formulation may be a tablet, capsule, caplet, etc. comprising a controlled release excipient and any desired amount of arginine α-ketoglutarate.

Another aspect of the invention is that it may be formulated with one or more additional prolyl and lysyl hydroxylase cofactors, e.g., ascorbic acid and iron donors.

Another aspect of the invention is a method of treatment whereby sustained low levels of arginine α-ketoglutarate blood serum over long periods continually stimulate basal prolyl hydroxylase and lysyl hydroxylase activity.

These and other objects, aspects, advantages, and features of the invention will become apparent to those persons skilled in the art upon reading the details of the invention as more fully described below.

DETAILED DESCRIPTION OF THE INVENTION

Before the present, formulations, methods and components used therein are disclosed and described, it is to be understood that this invention is not limited to particular compounds, excipients or formulations as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided are subject to change if it is found that the actual date of publication is different from that provided here.

Definitons

The term "arginine α-ketoglutarate" is intended to mean arginine α-ketoglutarate which is a salt also known as arginine 2-ketoglutarate, arginine 2-oxoglutamate, and arginine 2-oxopentanedioic acid. Unless specified, the term covers the racemic mixture as well as any other (non-50/50) mixture of the enantiomers including substantially pure forms of either the R-(+) or the S-(−) enantiomer. Further, unless specified otherwise the term covers pharmaceutically acceptable salts (e.g. Na and K salts) and amides, esters and metabolites of the acid. In referring to pharmaceutically acceptable salts the term is intended to encompass a conventional term of pharmaceutically acceptable acid addition salts which refer to salts which retain the biological effectiveness and properties of the free-base form of the acid and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malconic acid, succinic acid, maleic acid, fumaric, tartaric acid, citric acid, benzoic acid, cinnamic acid, mandelic acid, methanesulfonic acid, ethanesulfonic acid, p-toluenesulfonic acid, salicylic acid and the like. The same is true with respect to amides, esters and metabolites that is those forms which can be formed and maintain biological effectiveness and not have significant undesirable biological properties.

The term "excipient material" is intended to mean any compound forming a part of the formulation which is intended to act merely as a carrier, i.e., not intended to have biological activity itself.

The term "chemical degradation" is intended to mean that the arginine α-ketoglutarate active ingredient is subjected to a chemical reaction which disrupts its biological activity.

The terms "treating" and "treatment" and the like are used herein to generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease and/or its symptoms or conditions. The invention is directed towards treating patient's symptoms from glutamate dehydrogenase deficiency and depressed prolyl hydroxylase and lysyl hydroxylase activity. The present invention is involved in preventing, inhibiting, or relieving adverse effects attributed to glycation of proteins characteristic of atherosclerosis, cataract formation, retinopathy, and aging.

The term "quick release formulation" refers to a conventional oral dosage formulation. Such a formulation may be a tablet, capsule or the like designed to provide for substantially immediate release of the active ingredient and includes enteric coated oral formulation which provide some initial protection to the active ingredient and thereafter allow substantially immediate release of substantially all the active ingredient. A quick release formulation is not formulated in a manner so as to obtain a gradual, slow, or controlled release of the active ingredient.

Formulation in General

The formulation of the invention is preferably an oral dosage formulation which may be in any suitable oral form including tablets, capsules, caplets, suspensions, etc. The dosage may be of any desired size in terms of the arginine α-ketoglutarate active ingredient. However, sizes in a range of about 50 mg to about 1,000 mg are generally used, and are preferably in the range of about 100 mg to about 500 mg and more preferably about 300 mg. The amount a patient will need to obtain an optimum therapeutical effect will vary with a number of factors known to those skilled in the art, e.g., the size, age, weight, sex and condition of the patient. The patient may begin with daily doses of about 300 mg and determine, for example, if the effects of glutamate dehydrogenase deficiency has been offset. If the desired results are not obtained in one week, the daily dosage amount can be increased in increments of 100 to 300 mg/day up to any useful amount, e.g., 2,000 mg/day. A suggested dosage is to administer two 300 mg tablets in the morning and administer one 300 mg tablet four hours later and repeat daily over five or more days. The larger initial dosage has been found effective in obtaining a desired effect which after being obtained can be maintained by a lower dose. Thus, a biological system may be "kick started" by a high therapeutic level and then maintained at a lower level which is also therapeutic in terms of obtaining a desired result.

A typical formulation contains about 50–70% by weight arginine α-ketoglutarate active ingredient with the remainder being excipient material. Preferably the formulation comprises 55% to 65% active ingredient and more preferably about 60% active ingredient by weight. Thus, a particularly preferred oral formulation of the invention comprises about 300 mg of arginine α-ketoglutarate and about 200 mg of excipient material. Human patients generally eat during the day and sleep at night. Eating causes increased glucose levels. Accordingly, it is generally preferable to give a larger dose of arginine α-ketoglutarate at the beginning of the day. This may include two 300 mg tablets or a single 600 mg tablet. Later in the day (about 4 hours later) the patient will take an additional 300 mg for a typical daily dose of about 900 mg for a 70 kg man.

The formulation is characterized by (a) protecting the active ingredient from chemical degradation in a patient's gastrointestinal tract and (b) releasing the active ingredient in a controlled manner. By gradually releasing the active ingredient, the serum levels of arginine α-ketoglutarate obtained are (1) lower than those obtained with single injectable dose or a non-controlled release formulation; and (2) maintained over longer periods of time at a therapeutic level than obtained with single injectable dose or a non-controlled release formulation. Specifically, a formulation of the invention releases active ingredient so as to obtain a blood serum level in a human patient in a range of about 25 to about 75 ng/ml of plasma. The range is preferably about 35 to about 65 ng/ml of plasma and more preferably about 50 ng/ml of plasma ±5%.

Arginine α-ketoglutarate is characterized as (1) non-toxic at relatively high levels, i.e., levels well in excess of therapeutic levels; and (2) quickly metabolized by human patients. The present invention relies in part on the discovery that arginine α-ketoglutarate provides desirable therapeutic results even at very low levels provided those low levels are maintained over an extended period of time; whereas therapeutic results are not obtained (even with higher levels) if the therapeutic level is not maintained over a sufficient period of time. Further, the present invention relies in part on the discovery that therapeutic results are further improved if the formulation is delivered over a period of five or more days, preferably thirty or more consecutive days with long periods of therapeutic levels of arginine α-ketoglutarate being obtained on each of the days.

One aspect of the invention is that a range of highly desirable therapeutic effects are obtained even when the arginine α-ketoglutarate blood serum levels are maintained in a range well below those previous used. The present invention could obtain desired therapeutics effects with higher levels of arginine α-ketoglutarate in blood serum. However, at least minimum levels would need to be constantly maintained over a long period of time (4 hours or more per day) for a plurality of days to obtain the desired results. When the oral dosage form is designed to obtain the lowest possible therapeutic level over the longest possible time period the results obtained are maximized and the amount of drug needed is minimized.

The arginine α-ketoglutarate blood plasma level obtained via the present invention is insufficient to obtain a desired therapeutic effect if that level is maintained for only a short period of time, e.g., 4 hours or less. However, by using the controlled release formulation of the invention these lower arginine α-ketoglutarate blood plasma levels can be maintained over 8 hours or more, preferably over 12 hours or more and more preferably over 16 hours or more per day. Further, those arginine α-ketoglutarate blood plasma levels over these periods of time are repeatedly obtained over a period of days, preferably weeks or months and more preferably continuously over any period during which the patient would benefit from, for example, the substance's inhibition of protein glycation—which may be the remainder of the patient's life.

To obtain the desired results, a formulation of the invention includes a sufficient amount of arginine α-ketoglutarate such that it is capable of releasing enough arginine α-ketoglutarate per unit of time to obtain the desired arginine α-ketoglutarate serum levels while compensating for arginine α-ketoglutarate which is metabolized. To obtain the desired results the formulation may immediately and quickly provide an initial release of arginine α-ketoglutarate and thereafter provide a gradual release which slows over the useful life of the formulation. However, the release may be gradual from the beginning. In either case, there is a gradual slowing of the rate of release which is compensated for in that some of the previously released arginine α-ketoglutarate remains in the blood serum unmetabolized.

A preferred oral formulation is a tablet which is designed to dissolve gradually over a period of about 8 hours. As the tablet dissolves, its reduced size will release smaller and smaller amounts of arginine α-ketoglutarate per unit of time. However, because the individuals system already contains a therapeutic level of arginine α-ketoglutarate, the slower release rate is sufficient to match the rate of arginine α-ketoglutarate being metabolized and such will result in maintaining a relatively constant therapeutic level. At the end of the time when release of arginine α-ketoglutarate is no longer taking place (e.g., about 4 to 8 hours), another tablet is administered and the process is repeated. To obtain the benefits of the invention, the process is continually repeated over a plurality of days, weeks, months or years. By maintaining a minimal arginine α-ketoglutarate blood serum level over time, a patient's symptoms arising from a genetic glutamate dehydrogenase deficiency and depressed prolyl hydroxylase and lysyl hydroxylase activity would be alleviated. Likewise, those patients at increased risk for atherosclerosis, cataract formation, and retinopathy would have lowered their chances of pathogenesis.

Excipient Material

Examples provided here show that formulations of the invention may comprise different amounts and ratios of active ingredient and excipient material. Further, different excipients can be used. Particularly preferred excipients and amounts used are recited in the Examples. However, upon reading the disclosure those skilled in the art will come to understand the general concepts of the invention and will recognize that other excipients, amounts, ratios and combinations might be used to obtain the results first shown here.

The type and amount of excipient material is added to obtain a formulation having certain characteristics. First, the resulting formulation protects the active ingredient from chemical degradation in the patient's gastrointestinal tract. A formulation of pure, unprotected arginine α-ketoglutarate is not part of the scope of the present invention in that pure arginine α-ketoglutarate is degraded to some degree in the gastrointestinal tract. Although the formulation need not protect 100% of the arginine α-ketoglutarate from degradation to come within the scope of the invention, it should protect at least 90% or more, preferably 95% or more and more preferably 99% or more of the arginine α-ketoglutarate from degradation. Although multiple doses of an oral formulation could be taken it is preferable to design the dosage such that a single dose is taken at each dosing event— preferably three times a day and more preferably twice a day. The better the active ingredient is protected from degradation the less active ingredient is needed in the original dosage thereby reducing manufacturing costs and increasing profits. The formulation must protect at least as much of the dose as is needed to obtain a pharmacological effect and preferably obtain the desired treatment results, e.g., maintaining a desired arginine α-ketoglutarate serum level needed to compensate for genetic glutamate dehydrogenase deficiency.

Another characteristic of the formulation is that it does not release all of the active ingredient at one time but rather releases the active ingredient gradually over time at a controlled rate of release which rate is preferably constant over 4 hours or more. This is particularly important because a desired level of arginine α-ketoglutarate in blood serum must be maintained over a long period to obtain the desired effect. If all of the arginine α-ketoglutarate is released at once, it will all enter the circulatory system at once and be metabolized in the liver thereby causing the arginine α-ketoglutarate serum level to drop below the desired level. When this occurs, the compensation for glutamate dehyrogenase deficiency would be suboptimal.

Typical Formulations

A typical formulation of the invention will contain about 50% to about 70% by weight of arginine α-ketoglutarate and a particularly preferred formulation will comprise 60% by weight of arginine α-ketoglutarate. Assuming a formulation with about 50 to about 66.7% by weight of arginine α-ketoglutarate with the remaining being excipient material, there are a number of possible components which could be used to make up the remainder of the formulation A generalized and specific description of such is provided below:

| | | |
|---|---|---|
| (1) | arginine α-ketoglutarate | 60% |
| | organic polymer | 40% |
| | TOTAL | 100% |
| (2) | arginine α-ketoglutarate | 60% |
| | organic polymer | 34.5% |
| | inorganics | 5.5% |
| | TOTAL | 100% |
| (3) | arginine α-ketoglutarate | 60% |
| | organic polymer | 30%–40% |
| | inorganics | 10% or less |
| | TOTAL | 100% |
| (4) | arginine α-ketoglutarate | 60% |
| | microcrystalline cellulose | 14% |
| | cellulose acetate phthalate aqueous dispersion | 15% |
| | polyvinylpyraolidone | 3% |
| | ethyl acetate | 2.5% |
| | hydrous magnesium silicate (talc) | 1% |
| | carboxy methyl ether | 4% |
| | magnesium stearate | 0.5% |
| | TOTAL | 100% |
| (5) | arginine α-ketoglutarate | 60% |
| | microcrystalline cellulose | 10–30% |
| | cellulose acetate phthalate aqueous dispersion | 5–25% |
| | polyvinylpyraolidone | 1–5% |
| | ethyl acetate | 1–5% |
| | hydrous magnesium silicate (talc) | 0.5–3% |
| | carboxy methyl ether | 1–5% |
| | magnesium stearate | 0.5–1.5% |
| | TOTAL | 100% |
| (6) | arginine α-ketoglutarate | 60% |
| | microcrystalline cellulose, NF (Avicel PH 101) | 14% |
| | Aquacoat CPD-30 (30% solids w/w) | 15% |
| | Plasdone K29/32, USP | 3% |
| | Carbopol 974P, NF | 2.5% |
| | Talc, USP | 1.0% |
| | croscarmellose sodium, NF (Ac, di-Sol) | 4.0% |
| | Magnesium Stearate, NF | 0.5% |
| | TOTAL | 100% |

| | | |
|---|---|---|
| (7) | arginine α-ketoglutarate | 60% |
| | microcrystalline cellulose, NF (Avicel PH 101) | 10–30% |
| | Aquacoat CPD-30 (30% solids w/w) | 5–25% |
| | Plasdone K29/32, USP | 1–5% |
| | Carbopol 974P, NF | 1–5% |
| | Talc, USP | 0.5–3% |
| | croscarmellose sodium, NF (Ac, di-Sol) | 1–5% |
| | Magnesium Stearate, NF | 0.5–1.5% |
| | TOTAL | 100% |
| (8) | arginine α-ketoglutarate | 67% |
| | Di-Calcium Phosphate | 15.1% |
| | Zein | 2.1% |
| | Pectin | 4% |
| | Glycerin | 6.5% |
| | Alginate (Satialgine) | 3.3% |
| | PVAP | 2% |
| | TOTAL | 100% |
| (9) | arginine α-ketoglutarate | 60% |
| | Poly-DL-lactide-co-glycolide (PLG) | 40% |
| | TOTAL | 100% |
| (10) | arginine α-ketoglutarate | 60% |
| | hydroxypropyl methylcellulose | 30% |
| | Spray-dried lactose | 9.5% |
| | Magnesium stearate | 0.5% |
| | TOTAL | 100% |
| (11) | arginine α-ketoglutarate | 60–65% |
| | hydroxypropyl methylcellulose | 20–30% |
| | lactose | 5–15% |
| | microcrystalline cellulose | 4–6% |
| | titanium dioxide | 1–5% |
| | TOTAL | 100% |
| (12) | arginine α-ketoglutarate | 60% |
| | hydroxypropylcellulose | 40% |
| | TOTAL | 100% |
| (13) | arginine α-ketoglutarate | 60% |
| | hydroxypropylcellulose | 30% |
| | polyethylene oxide | 10% |
| | TOTAL | 100% |
| (14) | arginine α-ketoglutarate | 60% |
| | hydroxypropylcellulose | 15% |
| | hydroxypropyl methylcellulose | 25% |
| | TOTAL | 100% |
| (15) | arginine α-ketoglutarate | 65% |
| | hydroxypropyl methycellulose | 40% |
| | dibasic calcium phosphate | 6% |
| | colloidal silicon dioxide | 4% |
| | TOTAL | 100% |
| (16) | arginine α-ketoglutarate | 50–55% |
| | hydroxyalkylcellulose | 20–40% |
| | lactose | 5–15% |
| | microcrystalline cellulose | 4–6% |
| | titanium dioxide | 1–5% |
| | TOTAL | 100% |
| (17) | arginine α-ketoglutarate | 60% |
| | alkylcellulose | 30% |
| | spray-dried lactose | 9.5% |
| | magnesium stearate | 0.5% |
| | TOTAL | 100% |
| (18) | arginine α-ketoglutarate | 60% |
| | carboxymethylcellulose (hydrogel matrix) | 10% |
| | polyethylene oxide (hydrogel matrix) | 30% |
| | TOTAL | 100% |
| (19) | arginine α-ketoglutarate | 60% |
| | polyvinylpyrrolidone (hydrogel matrix) | 15% |
| | polyethylene glycol (hydrogel matrix) | 25% |
| | TOTAL | 100% |
| (20) | arginine α-ketoglutarate | 50–55% |
| | hydroxypropyl methylcellulose | 10–20% |
| | ethylcellulose | 10–20% |
| | lactose | 5–15% |
| | sorbitol | 4–6% |
| | silicon dioxide | 1–5% |
| | TOTAL | 100% |
| (21) | arginine α-ketoglutarate | 50% |
| | cellulose acetate butyrate | 30% |
| | starch | 9.5% |
| | magnesium stearate | 0.5% |
| | TOTAL | 100% |
| (22) | arginine α-ketoglutarate | 50% |
| | cellulose acetate phthalate | 30% |
| | cellulose acetate trimellitate | 10% |
| | mannitol | 9.5% |
| | calcium stearate | 0.5% |
| | TOTAL | 100% |
| (23) | arginine α-ketoglutarate | 50% |
| | polyvinylacetate phthalate | 35% |
| | hydroxypropylmethylcelluulose phthalate | 5% |
| | sucrose | 5–9% |
| | stearic acid | 1–5% |
| | TOTAL | 100% |
| (24) | arginine α-ketoglutarate | 50% |
| | methylcellulose | 35% |
| | hydroxypropylmethylcellulose | 5% |
| | glucose | 4% |
| | talc | 0.5% |
| | PEG 6000 | 0.5% |
| | TOTAL | 100% |
| (25) | arginine α-ketoglutarate | 60% |
| | polyethylene glycol | 20% |
| | poly(alkyl methacrylate) | 10% |
| | calcium stearate | 5% |
| | dibasic calcium phosphate | 3% |
| | poloxamers | 2% |
| | TOTAL | 100% |
| (26) | arginine -ketoglutarate | 60% |
| | Hydroxypropylmethylcellulose | 24% |
| | Pectin | 12% |
| | magnesium stearate | 4% |
| | TOTAL | 100% |
| (27) | arginine -ketoglutarate | 66.7% |
| | calcium sulfate | 17.3% |
| | zein | 1.3% |
| | alginate | 3.3% |
| | pectin | 4.0% |
| | glycerin | 6.7% |
| | magnesium stearate | 0.7% |
| | TOTAL | 100% |

Those skilled in the art will recognize that there are endless possibilities in terms of formulations and that a margin of error e.g., ±20% or more preferably ±10%, should be accounted for with each component. Even if the formulations are limited to the relatively few compounds shown above, the formulation could be changed in limitless ways by adjusting the ratios of the components to each other. The important feature of any formulation of the invention is that the arginine α-ketoglutarate be released in a controlled manner which makes it possible to maintain therapeutic levels of arginine α-ketoglutarate over a substantially longer period of time as compared to a quick release formulation. A particularly preferred formulation will quickly obtain a therapeutic level and thereafter decrease the rate of release to closely match the rate at which arginine α-ketoglutarate is being metabolized thereby maintaining a therapeutic level in the patient over a maximum period of time based on the amount of arginine α-ketoglutarate in the oral dosage formulation. Some general types of controlled release technology which might be used with the present invention are described below followed by specific preferred formulations.

Controlled Release Technology

Controlled release within the scope of this invention can be taken to mean any one of a number of extended release dosage forms. The following terms may be considered to be substantially equivalent to controlled release, for the purposes of the present invention: continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release. Further discussions of these terms may be found in Lesczek Krowczynski, *Extended-Release Dosage Forms,* 1987 (CRC Press, Inc.).

There are companies with specific expertise in drug delivery technologies including controlled release oral formulations such as Alza Corporation and Elan Pharmaceuticals, Inc. A search of patents, published patent applications and related publications will provide those skilled in the art reading this disclosure with significant possible controlled release oral formulations. Examples include the formulations disclosed in any of the U.S. Pat. No. 5,637,320 issued Jun. 10, 1997; U.S. Pat. No. 5,505,962 issued Apr. 9, 1996; U.S. Pat. No. 5,641,745 issued Jun. 24, 1997; and U.S. Pat. No. 5,641,515 issued Jun. 24, 1997. Although specific formulations are disclosed here and in these patents, the invention is more general than any specific formulation. This includes the discovery that by placing arginine α-ketoglutarate in a controlled release formulation which maintains therapeutic levels over substantially longer periods of time, as compared to quick release formulations, improved unexpected results are obtained.

The various controlled release technologies cover a very broad spectrum of drug dosage forms. Controlled release technologies include, but are not limited to physical systems and chemical systems.

Physical systems include, but are not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., nonerodible, erodible, environmental agent ingression, and degradable), and materials physically dispersed in non-porous, polymeric, or elastomeric matrices (e.g., nonerodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release may be found in Agis F. Kydonieus, *Controlled Release Technologies: Methods, Theory and Applications,* 1980 (CRC Press, Inc.).

Controlled release drug delivery systems may also be categorized under their basic technology areas, including, but not limited to, rate-preprogrammed drug delivery systems, activation-modulated drug delivery systems, feedback-regulated drug delivery systems, and site-targeting drug delivery systems.

In rate-preprogrammed drug delivery systems, release of drug molecules from the delivery systems "preprogrammed" at specific rate profiles. This may be accomplished by system design, which controls the molecular diffusion of drug molecules in and/or across the barrier medium within or surrounding the delivery system. Fick's laws of diffusion are often followed.

In activation-modulated drug delivery systems, release of drug molecules from the delivery systems is activated by some physical, chemical or biochemical processes and/or facilitated by the energy supplied externally. The rate of drug release is then controlled by regulating the process applied, or energy input.

In feedback-regulated drug delivery systems, release of drug molecules from the delivery systems may be activated by a triggering event, such as a biochemical substance, in the body. The rate of drug release is then controlled by the concentration of a triggering agent detected by a sensor in the feedback regulated mechanism.

In a site-targeting controlled-release drug delivery system, the drug delivery system targets the active molecule to a specific site or target tissue or cell. This may be accomplished, for example, by a conjugate including a site specific targeting moiety that leads the drug delivery system to the vicinity of a target tissue (or cell), a solubilizer that enables the drug delivery system to be transported to and preferentially taken up by a target tissue, and a drug moiety that is covalently bonded to the polymer backbone through a spacer and contains a cleavable group that can be cleaved only by a specific enzyme at the target tissue.

While a preferable mode of controlled release drug delivery will be oral, other modes of delivery of controlled release compositions according to this invention may be used. These include mucosal delivery, nasal delivery, ocular delivery, transdermal delivery, parenteral controlled release delivery, vaginal delivery, and intrauterine delivery.

There are a number of controlled release drug formulations that are developed preferably for oral administration. These include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems; and ion-exchange-controlled gastrointestinal delivery systems, which include cationic and anionic drugs. Additional information regarding controlled release drug delivery systems may be found in Yie W. Chien, *Novel Drug Delivery Systems,* 1992 (Marcel Dekker, Inc.). Some of these formulations will now be discussed in more detail.

Enteric coatings are applied to tablets to prevent the release of drugs in the stomach either to reduce the risk of unpleasant side effects or to maintain the stability of the drug which might otherwise be subject to degradation due to exposure to the gastric environment. Most polymers that are used for this purpose are polyacids that function by virtue or the fact that their solubility in aqueous medium is pH-dependent, and they require conditions with a pH higher then that which is normally encountered in the stomach.

One preferable type of oral controlled release structure is enteric coating of a solid or liquid dosage form. Enteric coatings promote the lipoates' remaining physically incorporated in the dosage form for a specified period when exposed to gastric juice. Yet the enteric coatings are designed to disintegrate in intestinal fluid for ready absorption. Delay of the lipoates' absorption is dependent on the rate of transfer through the gastrointestinal tract, and so the rate of gastric emptying is an important factor. Some investigators have reported that a multiple-unit type dosage form, such as granules, may be superior to a single-unit type. Therefore, in a preferable embodiment, the lipoates may be contained in an enterically coated multiple-unit dosage form. In a more preferable embodiment, the lipoate dosage form is prepared by spray-coating granules of a lipoate-enteric coating agent solid dispersion on an inert core material. These granules can result in prolonged absorption of the drug with good bioavailability.

Typical enteric coating agents include, but are not limited to, hydroxypropylmethylcellulose phthalate, methacryclic acid-methacrylic acid ester copolymer, polyvinyl acetate-phthalate and cellulose acetate phthalate. Akihiko Hasegawa, *Application of solid dispersions of Nifedipine with enteric coating agent to prepare a sustained-release dosage form*, Chem. Pharm. Bull. 33: 1615–1619 (1985). Various enteric coating materials may be selected on the basis of testing to achieve an enteric coated dosage form designed ab initio to have a preferable combination of dissolution time, coating thicknesses and diametral crushing strength. S. C. Porter et al., *The Properties of Enteric Tablet Coatings Made From Polyvinyl Acetate-phthalate and Cellulose acetate Phthalate*, J. Pharm. Pharmacol. 22:42p (1970).

On occasion, the performance of an enteric coating may hinge on its permeability. S. C. Porter et al., *The Permeability of Enteric Coatings and the Dissolution Rates of Coated Tablets*, J. Pharm. Pharmacol. 34: 5–8 (1981). With such oral drug delivery systems, the drug release process may be initiated by diffusion of aqueous fluids across the enteric coating. Investigations have suggested osmotic driven/rupturing affects as important release mechanisms from enteric coated dosage forms. Roland Bodmeier et al., *Mechanical Properties of Dry and Wet Cellulosic and Acrylic Films Prepared from Aqueous Colloidal Polymer Dispersions used in the Coating of Solid Dosage Forms*, Pharmaceutical Research, 11: 882–888 (1994).

Another type of useful oral controlled release structure is a solid dispersion. A solid dispersion may be defined as a dispersion of one or more active ingredients in an inert carrier or matrix in the solid state prepared by the melting (fusion), solvent, or melting-solvent method. Akihiko Hasegawa, *Super Saturation Mechanism of Drugs from Solid Dispersions with Enteric Coating Agents*, Chem. Pharm. Bull. 36: 4941–4950 (1998). The solid dispersions are also referred to as solid-state dispersions. The term "coprecipitates" may also be used to refer to those preparations obtained by the solvent methods.

Solid dispersions may be used to improve the solubilities and/or dissolution rates of poorly water-soluble lipoates. Hiroshi Yuasa, et al., *Application of the Solid Dispersion Method to the Controlled Release Medicine. III. Control of the Release Rate of Slightly Water-Soluble Medicine From Solid Dispersion Granules*, Chem. Pharm. Bull. 41:397–399 (1993). The solid dispersion method was originally used to enhance the dissolution rate of slightly water-soluble medicines by dispersing the medicines into water-soluble carriers such as polyethylene glycol or polyvinylpyraolidone, Hiroshi Yuasa, et al., *Application of the Solid Dispersion Method to the Controlled Release of Medicine. IV. Precise Control of the Release Rate of a Water-Soluble Medicine by Using the Solid Dispersion Method Applying the Difference in the Molecular Weight of a Polymer*, Chem. Pharm. Bull. 41:933–936 (1993).

The selection of the carrier may have an influence on the dissolution characteristics of the dispersed drug because the dissolution rate of a component from a surface may be affected by other components in a multiple component mixture. For example, a water-soluble carrier may result in a fast release of the drug from the matrix, or a poorly soluble or insoluble carrier may lead to a slower release of the drug from the matrix. The solubility of the lipoates may also be increased owing to some interaction with the carriers.

Examples of carriers useful in solid dispersions according to the invention include, but are not limited to, water-soluble polymers such as polyethylene glycol, polyvinylpyraolidone, or hydroxypropylmethyl-cellulose. Akihiko Hasegawa, *Application of Solid Dispersions of Nifedipine with Enteric Coating Agent to Prepare a Sustained-release Dosage Form*, Chem. Pharm. Bull. 33: 1615–1619 (1985).

Alternate carriers include phosphatidylcholine. Makiko Fujii, et al., *The Properties of Solid Dispersions of Indomethacin, Ketoprofen and Flurbiprofen in Phosphatidylcholine*, Chem. Pharm. Bull. 36:2186–2192 (1988). Phosphatidylcholine is an amphoteric but water-insoluble lipid, which may improve the solubility of otherwise insoluble lipoates in an amorphous state in phosphatidylcholine solid dispersions. See Makiko Fujii, et al., *Dissolution of Bioavailibility of Phenytoin in Solid Dispersion with Phosphatidylcholine*, Chem. Pharm. Bull 36:4908–4913 (1988).

Other carriers include polyoxyethylene hydrogenated castor oil. Katsuhiko Yano, et al., *In-Vitro Stability and In-Vivo Absorption Studies of Colloidal Particles Formed From a Solid Dispersion System*, Chem. Pharm. Bull 44:2309–2313 (1996). Poorly water-soluble lipoates may be included in a solid dispersion system with an enteric polymer such as hydroxypropylmethylcellulose phthalate and carboxymethylethylcellulose, and a non-enteric polymer, hydroxypropylmethylcellulose. See Toshiya Kai, et al., *Oral Absorption Improvement of Poorly Soluble Drug Using Soluble Dispersion Technique*, Chem. Pharm. Bull. 44:568–571 (1996). Another solid dispersion dosage form include incorporation of the drug of interest with ethyl cellulose and stearic acid in different ratios. Kousuke Nakano, et al., *Oral Sustained-Release Cisplatin Preparations for Rats and Mice*, J. Pharm. Pharmacol. 49:485–490 (1997).

There are various methods commonly known for preparing solid dispersions. These include, but are not limited to the melting method, the solvent method and the melting-solvent method.

In the melting method, the physical mixture of a drug in a water-soluble carrier is heated directly until it melts. The melted mixture is then cooled and solidified rapidly while rigorously stirred. The final solid mass is crushed, pulverized and sieved. Using this method a super saturation of a solute or drug in a system can often be obtained by quenching the melt rapidly from a high temperature. Under such conditions, the solute molecule may be arrested in solvent matrix by the instantaneous solidification process. A disadvantage is that many substances, either drugs or carriers, may decompose or evaporate during the fusion process at high temperatures. However, this evaporation problem may be avoided if the physical mixture is heated in a sealed container. Melting under a vacuum or blanket of an inert gas such as nitrogen may be employed to prevent oxidation of the drug or carrier.

The solvent method has been used in the preparation of solid solutions or mixed crystals of organic or inorganic compounds. Solvent method dispersions may prepared by dissolving a physical mixture of two solid components in a common solvent, followed by evaporation of the solvent. The main advantage of the solvent method is that thermal decomposition of drugs or carriers may be prevented because of the low temperature required for the evaporation of organic solvents. However, some disadvantages associated with this method are the higher cost of preparation, the difficulty in completely removing liquid solvent, the possible adverse effect of its supposedly negligible amount of the solvent on the chemical stability of the drug.

Another method of producing solid dispersions is the melting-solvent method. It is possible to prepare solid dispersions by first dissolving a drug in a suitable liquid solvent and then incorporating the solution directly into a melt of polyethylene glycol, obtainable below 70 degrees, without removing the liquid solvent. The selected solvent or dissolved lipoate may be selected such that the solution is not miscible with the melt of polyethylene glycol. The polymorphic form of the lipoate may then be precipitated in the melt. Such a unique method possesses the advantages of both the melting and solvent methods. Win Loung Chiou, et al., *Pharmaceutical Applications of Solid Dispersion Systems*, J. Pharm. Sci. 60:1281–1301 (1971).

Another controlled release dosage form is a complex between an ion exchange resin and the lipoates. Ion exchange resin-drug complexes have been used to formulate sustained-release products of acidic and basic drugs. In one preferable embodiment, a polymeric film coating is provided to the ion exchange resin-drug complex particles, making drug release from these particles diffusion controlled. See Y. Raghunathan et al., *Sustained-released drug delivery system I: Coded ion-exchange resin systems for phenylpropanolamine and other drugs*, J. Pharm. Sciences 70: 379–384 (1981).

Injectable micro spheres are another controlled release dosage form. Injectable micro spheres may be prepared by non-aqueous phase separation techniques, and spray-drying techniques. Micro spheres may be prepared using polylactic acid or copoly(lactic/glycolic acid). Shigeyuki Takada, *Utilization of an Amorphous Form of a Water-Soluble GPIIb/IIIa Antagonist for Controlled Release From Biodegradable Micro spheres*, Pharm. Res. 14:1146–1150 (1997), and ethyl cellulose, Yoshiyuki Koida, *Studies on Dissolution Mechanism of Drugs from Ethyl Cellulose Microcapsules*, Chem. Pharm. Bull. 35:1538–1545 (1987).

Other controlled release technologies that may be used in the practice of this invention are quite varied. They include SODAS, INDAS, IPDAS, MODAS, EFVAS, DUREDAS. SODAS are multi particulate dosage forms utilizing controlled release beads. INDAS are a family of drug delivery technologies designed to increase the solubility of poorly soluble drugs. IPDAS are multi particulate tablet formation utilizing a combination of high density controlled release beads and an immediate release granulate. MODAS are controlled release single unit dosage forms. Each tablet consists of an inner core surrounded by a semipermeable multiparous membrane that controls the rate of drug release. EFVAS is an effervescent drug absorption system. PRODAS is a family of multi particulate formulations utilizing combinations of immediate release and controlled release minitablets. DUREDAS is a bilayer tablet formulation providing dual release rates within the one dosage form. Although these dosage forms are known to one of skill, certain of these dosage forms will now be discussed in more detail.

INDAS was developed specifically to improve the solubility and absorption characteristics of poorly water soluble drugs. Solubility and, in particular, dissolution within the fluids of the gastrointestinal tract is a key factor in determining the overall oral bioavailability of poorly water soluble drug. By enhancing solubility, one can increase the overall bioavailability of a drug with resulting reductions in dosage. INDAS takes the form of a high energy matrix tablet, production of which is comprised of two distinct steps: the adensosine analog in question is converted to an amorphous form through a combination of energy, excipients, and unique processing procedures.

Once converted to the desirable physical form, the resultant high energy complex may be stabilized by an absorption process that utilizes a novel polymer cross-linked technology to prevent recrystallization. The combination of the change in the physical state of the lipoate coupled with the solubilizing characteristics of the excipients employed enhances the solubility of the lipoate. The resulting absorbed amorphous drug complex granulate may be formulated with a gel-forming erodible tablet system to promote substantially smooth and continuous absorption.

IPDAS is a multi-particulate tablet technology that may enhance the gastrointestinal tolerability of potential irritant and ulcerogenic drugs. Intestinal protection is facilitated by the multi-particulate nature of the IPDAS formulation which promotes dispersion of an irritant lipoate throughout the gastrointestinal tract. Controlled release characteristics of the individual beads may avoid high concentration of drug being both released locally and absorbed systemically. The combination of both approaches serves to minimize the potential harm of the lipoates with resultant benefits to patients.

IPDAS is composed of numerous high density controlled release beads. Each bead may be manufactured by a two step process that involves the initial production of a micromatrix with embedded lipoates and the subsequent coating of this micromatrix with polymer solutions that form a rate limiting semipermeable membrane in vivo. Once an IPDAS tablet is ingested, it may disintegrate and liberate the beads in the stomach. These beads may subsequently pass into the duodenum and along the gastrointestinal tract, preferably in a controlled and gradual manner, independent of the feeding state. Lipoate release occurs by diffusion process through the micromatrix and subsequently through the pores in the rate controlling semipermeable membrane. The release rate from the IPDAS tablet may be customized to deliver a drug-specific absorption profile associated with optimized clinical benefit. Should a fast onset of activity be necessary, immediate release granulate may be included in the tablet. The tablet may be broken prior to administration, without substantially compromising drug release, if a reduced dose is required for individual titration.

DUREDAS is a bilayer tableting technology that may be used in the practice of the invention. DUREDAS was developed to provide for two different release rates, or dual release of a drug from one dosage form. The term bilayer refers to two separate direct compression events that take place during the tableting process. In a preferable embodiment, an immediate release granulate is first compressed, being followed by the addition of a controlled release element which is then compressed onto this initial tablet. This may give rise to the characteristic bilayer seen in the final dosage form.

The controlled release properties may be provided by a combination of hydrophilic polymers. In certain cases, a rapid release of the arginine α-ketoglutarate may be desirable in order to facilitate a fast onset of therapeutic affect. Hence one layer of the tablet may be formulated as an immediate release granulate. By contrast, the second layer of the tablet may release the drug in a controlled manner, preferably through the use of hydrophilic polymers. This controlled release may result from a combination of diffusion and erosion through the hydrophilic polymer matrix.

A further extension of DUREDAS technology is the production of controlled release combination dosage forms. In this instance, two different arginine α-ketoglutarate compounds may be incorporated into the bilayer tablet and the release of drug from each layer controlled to maximize therapeutic affect of the combination.

The arginine α-ketoglutarate of the invention can be incorporated into any one of the aforementioned controlled released dosage forms, or other conventional dosage forms. The amount of arginine α-ketoglutarate contained in each dose can be adjusted to meet the needs of the individual patient and the indication. One of skill in the art reading this disclosure will readily recognize how to adjust the level of arginine α-ketoglutarate and the release rates in a controlled release formulation, in order to optimize delivery of arginine α-ketoglutarate and its bioavailability.

Therapeutic Indications

The controlled release arginine α-ketoglutarate formulations of the present invention can be used to obtain a wide range of desirable effects. Further, the invention can be used in the treatment of diseases which involve glutamate dehydrogenase deficiency, depressed prolyl hydroxylase and lysyl hydroxylase activity. Further, the invention is useful in the treatment of various adverse effects on the eyes and skin when the adverse effect are due to accumulation of protein glycation. Maintaining substantially constant levels of arginine α-ketoglutarate provides a long term antioxidant effect which assists in immunomodulation.

Because of the very minimal toxicity of arginine α-ketoglutarate, it can be given to a wide range of patients which have different conditions from mild to serious without fear of adverse effects. Further, the controlled release formulations taught here are even safer than quick release formulations in that serum levels obtained are low compared to quick release formulations.

The data provided here do not show specific treatments of many of the diseases or symptoms mentioned above. However, the invention is believed to be responsible for obtaining a wide range of beneficial effects particularly when the controlled release formulation is administered to patients over long periods of time, i.e., weeks, months and years. By maintaining substantially constant therapeutic levels of arginine α-ketoglutarate in the blood over very long periods of time a range of desirable physiological results are obtained. Stated differently, by continually maintaining the constant therapeutic serum levels of the powerful antioxidant and preventing protein glycation, the pathogenesis of atherosclerosis, cataracts and retinopathy is prevented.

EXAMPLES

With reference to Table 1, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Before formulating, a check should be made of the room and equipment in order to verify that the cleaning procedure has been performed and approved. Weigh and charge α-Arginine α-ketoglutarate and calcium phosphate, then blend in Hobart at speed 1. Dissolve zein in 250 mL of IPA and 50 mL of DW using the Silverson until sell dispersed. Granulate arginine with zein and blend at speed 1 for 15 minutes until granulate formed. Material should be light granulate, with yellow color blended for 10–20 minutes. While mixing the zein granulate, suspend pectin in glycerin using Silveron. Pour the smooth pectin glycerin mixture into zein granulate and blend for 15–20 minutes. Finally, disperse the Stagaline-20 in 800 mL of 0.05M KH2PO4 at pH 6.8 until smooth free flowing material is obtained, then add this to granulate at speed 2 and blend for 20 minutes. Continue the blending at speed 2 until well dispersed granulate is formed. After the material has been thoroughly dried, place it through a fitzmill screen #093 with added magnesium stearate. Compress the material into tablets having a weight of 1500 mg with a fracture force of ±15 kg and with a disintegration time be >1 hour.

Table 1 is a data table showing the dissolution of a formulation of the invention which is a controlled release oral formulation of arginine α-ketoglutarate over time with time shown in hours.

TABLE 1

Assay: Dissolution

| Timepoint | mg Arginine Released/tab | mg Arginine α-keto glutarate Released/tab | % of "Infinity" Released |
|---|---|---|---|
| 0.5 hr | 90 | 165 | 16.5 |
| 1 hr | 138 | 254 | 25.5 |
| 2 hr | 226 | 416 | 41.7 |
| 3 hr | 308 | 566 | 56.8 |
| 4 hr | 374 | 688 | 69.0 |
| 5 hr | 425 | 781 | 78.3 |
| 6 hr | 467 | 859 | 86.2 |
| 7 hr | 508 | 934 | 93.7 |
| 8 hr | 538 | 989 | 99.2 |
| Infinity | 542 | 997 | 100.0 |

| | Desired Tablet Wt.: 1500.0 mg | | |
|---|---|---|---|
| | Desired Batch Size: 1.0 kg | | |
| Ingredients | Percent | mg per Tablet | kg per Batch |
| 1. Arginine AKG | 66.7 | 1000.0 | 0.667 |
| 2. Calcium Sulfate | 17.3 | 259.5 | 0.173 |
| 3. Zein | 1.3 | 19.5 | 0.013 |
| 4. Alginate (Satagiline) | 3.3 | 49.5 | 0.033 |
| 5. Pectin | 4.0 | 60.0 | 0.040 |
| 6. Glycerin | 6.7 | 100.5 | 0.067 |
| 7. Magnesium Stearate | 0.7 | 10.5 | 0.007 |
| Total | 100 | 1499.5 | 0.000 |

The instant invention is shown and described herein in what is considered to be the most practical, and preferred embodiments. It is recognized, however, that departures may be made therefrom, which are within the scope of the invention, and that obvious modifications will occur to one skilled in the art upon reading this disclosure.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A controlled release oral dosage formulation, comprising:

about 50–70% arginine α-ketoglutarate; and an excipient material comprising the remainder of the formulation;

wherein excipient is chosen from microcrystalline cellulose, hydroxypropylmethyl cellulose, ethylcellulose, cellulose acetate butyrate, cellulose acetate phthalate, polyvinyl acetate phthalate, hydroxypropylmethyl cellulose phthalate, polyethylene oxide, polyvinylpyrrolidone, polyethylene glycol, zein, poly-DL-lactide-co-glycolide, dicalcium phosphate, calcium sulfate, and mixture thereof;

wherein the formulation is characterized by releasing the arginine α-ketoglutarate in a manner so as to increase a period of time over which a therapeutic level of arginine α-ketoglutarate is maintained as compared to a quick release formulation.

2. The formulation of claim 1, wherein the releasing is in a manner which maintains the therapeutic level of arginine α-ketoglutarate for a period of time which is 10% or more longer as compared to a quick release formulation.

3. The formulation of claim 1, wherein the releasing is in a manner which maintains the therapeutic level of arginine α-ketoglutarate for a period of time which is 50% or more longer as compared to a quick release formulation.

4. The formulation of claim 1, wherein the releasing is in a manner which maintains the therapeutic level of arginine α-ketoglutarate for a period of time which is 100% or more longer as compared to a quick release formulation.

5. The formulation of claim 1, wherein the releasing is in a manner which maintains the therapeutic level of arginine α-ketoglutarate for a period of time which is 200% or more longer as compared to a quick release formulation.

6. The formulation of claim 1, wherein the releasing is sufficiently slow that a maximum level of arginine α-ketoglutarate obtained is less as compared to a maximum level obtained with a quick release formulation.

7. The formulation of claim 1, wherein the releasing is sufficiently slow that a maximum level of arginine α-ketoglutarate obtained is 50% or more, less as compared to a maximum level obtained with a quick release formulation.

8. The formulation of claim 1, wherein the releasing of arginine α-ketoglutarate is at a rate of about 25% or less per hour after an initial release rate within 30 minutes following administration as compared to a quick release formulation.

9. The formulation of claim 1, wherein the releasing of arginine α-ketoglutarate is at a rate of about 50% or less per hour after an initial release rate within 30 minutes following administration as compared to a quick release formulation.

10. A method of treating atherosclerosis in a human patient, comprising:

administering to a human patient a controlled release formulation of arginine α-ketoglutarate which formulation is characterized by maintaining a therapeutic level of arginine α-ketoglutarate in the patient's circulatory system over a period of time greater than that obtained with a quick release formulation; and repeating the administering on three or more consecutive days thereby maintaining a therapeutic level of arginine α-ketoglutarate in the patient's circulatory system over a therapeutically effective period of time on three or more consecutive days.

11. The method of claim 10, wherein the therapeutic level is maintained over a period of time which is 10% or more than that obtained with a quick release formulation and further wherein the repeating is over thirty or more consecutive days.

12. The method of claim 10, wherein the therapeutic level is maintained over a period of time which is 100% or more than that obtained with a quick release formulation and further wherein the repeating is over thirty or more consecutive days.

13. The method of claim 12, wherein the therapeutic level is a level sufficient to obtain measurable increase in prolyl hydroxylase and lysyl hydroxylase activity in a human patient.

14. The method of claim 12, wherein the therapeutic level is a level sufficient to prevent protein glycation associated with atherosclerosis, cataract formation and retinopathy.

* * * * *